United States Patent [19]

Czytko et al.

[11] Patent Number: 4,882,277
[45] Date of Patent: Nov. 21, 1989

[54] CONTINUOUS PROCESS FOR PREPARING ORGANIC ACIDS BY FERMENTATION

[75] Inventors: Michael Czytko, Bochum, Fed. Rep. of Germany; Kiyoshi Ishii, Himeji; Kimitoshi Kawai, Hyogo, both of Japan

[73] Assignee: Hüls Aktiengesellschaft, Marl, Fed. Rep. of Germany

[21] Appl. No.: 943,698

[22] Filed: Dec. 19, 1986

[30] Foreign Application Priority Data

Dec. 20, 1985 [JP] Japan .................. 60-287521

[51] Int. Cl.$^4$ .......................... C12P 7/40; C12P 7/56
[52] U.S. Cl. .................................. 435/136; 435/139; 204/182.4
[58] Field of Search .............................. 435/136, 139; 204/182.3, 182.4, 182.5, 182.6, 301

[56] References Cited

U.S. PATENT DOCUMENTS

| | | | |
|---|---|---|---|
| 2,829,095 | 4/1958 | Oda et al. | 204/98 |
| 3,873,425 | 3/1975 | Kobayashi et al. | 195/37 |
| 3,964,985 | 6/1976 | Giuffrida | 204/301 |
| 4,110,175 | 8/1978 | Ahlgren et al. | 204/180 |
| 4,454,012 | 6/1984 | Bachot et al. | 204/182.4 |
| 4,486,283 | 12/1984 | Tejeda | 204/301 |

FOREIGN PATENT DOCUMENTS

| | | |
|---|---|---|
| 1957395 | 11/1968 | Fed. Rep. of Germany . |
| 1564115 | 3/1968 | France . |
| 2555200 | 5/1985 | France .................. 435/139 |
| 56-50958 | of 1981 | Japan . |
| 58-32959 | of 1983 | Japan . |

OTHER PUBLICATIONS

CA 84:149221q, Patent Abstract, Fedotkin, I.M. et al. (U.S.S.R.).
Hongo et al., Applied and Environmental Microbiology, 52(2):314 (1986).
Patent Abstract of Japan, JP 52-136985.
Voss, J. Membrane Science, 27(2):165-171.

Primary Examiner—Michael S. Marcus
Assistant Examiner—Rebekah Griffith
Attorney, Agent, or Firm—Bernard, Rothwell & Brown

[57] ABSTRACT

Organic acids are prepared by fermentation and then separated from the fermentation broth by means of an electrodialysis.

The present process does not require an addition of an alkali. The organic acids are recovered as free acids with high purity and at high yields.

8 Claims, 1 Drawing Sheet

CONTINUOUS PROCESS FOR PREPARING ORGANIC ACIDS BY FERMENTATION

BACKGROUND OF THE INVENTION

Organic acids prepared from saccharides such as starch, sucrose, or glucose, or from n-paraffines by fermentation include lactic, gluconic, kojic, citric, succinic, malic, and itaconic acids. In the process for preparing them, the step of fermentation is relatively simple, but the steps of recovery and purification of a product, an organic acid, are complicated with poor efficiency. For example, recovery of a representative organic acid, lactic acid, is made as follows. A cell body is filtered out of a fermentation liquor after the reaction has been completed. For increasing the filtration efficiency, it is necessary to coagulate a cell body and dissolved proteins in the filtrate by heating. Subsequently, sulfuric acid is added to the filtrate to precipitate an alkali, such as calcium carbonate or calcium hydroxide, which was added to the fermentation liquor to adjust the pH thereof, as a sulfate, followed by filtration. The filtrate is then freed from impurities, such as unreacted raw material, with an activated charcoal. The resulting solution is subjected to, for example, purification with an ion exchange resin, distillation in the form of a corresponding methyl ester followed by hydrolysis, or extraction with a solvent followed by extraction with water to obtain a free acid.

To improve the above-mentioned process involving a number of complicated steps, there has been proposed a process for continuously conducting fermentation by continuously recovering a formed organic acid from a fermentation liquor according to electrodialysis using an ion exchange membrane. More specifically, Japanese Patent Publication No. 50958/1981 discloses a continuous fermentation process comprising discharging a fermentation liquor from an itaconic acid fermenter at a constant rate, filtering a cell body, removing high molecular weight impurities by ultrafiltration, converting itaconic acid into an alkali metal salt thereof, and supplying the salt to an electrodialysis stack for separation of the itaconate from the fermentation liquor while returning the liquor form which the itaconate has been removed to the fermenter after addition of a substrate thereto. The disclosure mentions advantages that accumulation of fermentation-inhibiting substances in the fermentation system can be prevented by continuously withdrawing the product to enable the fermentation to be continuously carried out with high efficiency, and that the withdrawn itaconate is so pure that it can be readily separated by precipitation. On the other hand, Japanese Patent Publication No. 32959/1983 discloses a process comprising removing a cell body from a fermentation liquor of glutamic acid, converting the glutamic acid into a salt with an alkali, and recovering the salt by electrodialysis.

PROBLEMS TO BE SOLVED BY THE INVENTION

In any one of these processes, however, the organic acid is recovered in the form of a salt thereof. Thus the pH adjustment of the fermentation liquor by supplementing an alkali is necessary. Where the desired end product is a salt of an organic acid, these processes are satisfactory. However, where the desired end product is a free acid, the step of acid decomposition is needed, disadvantageously leading to an increase in the number of steps.

An object of the present invention is to provide a process for fermenting a saccharide to form an organic acid such as gluconic or lactic acid, wherein an organic acid is recovered in a form of a free acid by continuous supply of a fermentation liquor to an electrodialysis stack, which supply also may realize prevention of inhibition by the products as well as pH adjustment at the time of fermentation, thus enabling the fermentation to be continuously carried out with high efficiency without addition of an alkali liquid.

SUMMARY OF THE INVENTION

Means for Solving the Problems

In accordance with the present invention, there is provided a continuous process for preparing an organic acid by fermentation, which is characterized by passing and circulating part of a fermentation liquor from a fermenter through an electrodialysis stack to recover a concentrated organic acid.

DETAILED DESCRIPTION OF THE PREFERRED EMBODIMENTS

The organic acid obtained according to the process of this invention is an organic acid prepared from a saccharide such as starch, sucrose, or glucose, or from n-paraffines by fermentation. Examples of such organic acids include lactic, gluconic, kojic, citric, and succinic acids. The organic acid producing microorganisms which can be used include *Streptococcus lactis*, *Lactobacillus delbrueckii*, *Gluconobacter roseus*, *Aspergillus niger*, *Aspergillus oryzae*, *Citromyces pfefferianus*, *Brevibacterium flavum*, *Aspergillus flavus* and *Aspergillus itaconicus*. The composition of a fermentation medium where an organic acid is produced using the above-mentioned microorganisms may be any one which is suitable for an organic acid producing microorganism to be used. It essentially comprises one or more saccharides such as glucose, fructose, sucrose, maltose, a starch hydrolyzate, and substances containing a saccharide, such as molasses; one or more inorganic salts such as magnesium sulfate, ammonium sulfate, calcium primary phosphate, and ferrous sulfate if desired; and at least one growth promoting component selected from among yeast extract, peptone, meat extract, and a soybean powder.

A temperature suitable for each species of microorganism used is employed as the fermentation temperature. It is usually about 25° to 60° C.

These organic acid producing microorganisms have an acid sensitivity. Thus the medium is required to have a pH of 3.0 to 9.0. The anion exchange membrane and the cation exchange membrane to be used in the process of this invention may be any one available commercially. Examples of the cation exchange membrane include "Neosepta® CL-25T" and "Neosepta® CMS" (manufactured by Tokuyama Soda Co., Ltd.) and "Selemion CMV" (manufactured by Asahi Glass Co., Ltd.). Examples of the anion exchange membrane include "Neosepta® ACH-45T", "Neosepta® AM-3", "Selemion® AMV", "Selemion® AMP", and "Selemion® AMF". "Neosepta® CMS" and "Neosepta® AM-3" are preferred since the amount of solutes other than the organic acid formed in fermentation which leak out by diffusion is small. Especially preferred anion exchange membranes adjacent to the cathode chamber are "Selemion ® AMP" and "Selemion ® AMF" from the standpoint of alkali resistance.

Figure 1:
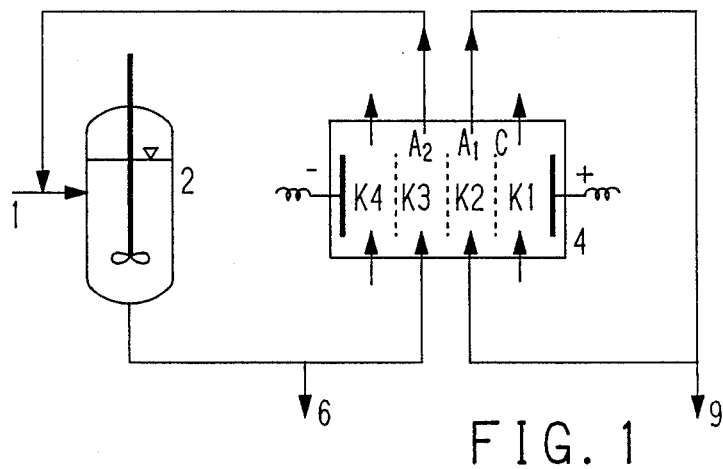
FIG. 1 shows a four compartment electrodialysis stack for preparing organic acids by fermentation.
Figure 2:
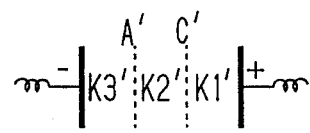
FIG. 2 shows a three compartment electrodialysis stack.
Figure 3:
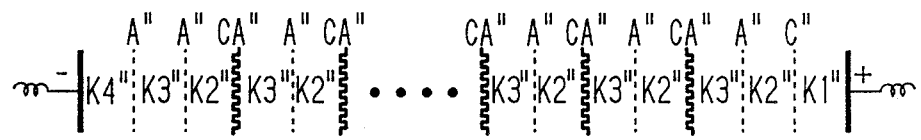
FIG. 3 shows a multi-compartment electrodialysis stack.

The electrodialysis of the process of this invention by use of any one of the electrodialysis stacks shown in FIG. 1 through FIG. 3 is illustrated as follows.

The electrodialysis stack 4 shown in FIG. 1 includes four compartments partitioned by three ion exchange membranes, i.e., a cation exchange membrane C, an anion exchange membrane $A_1$, and an anion exchange membrane $A_2$ in this order from the side of an anode. An aqueous acid solution is circulated through an anode cell (the first compartment $K_1$), while an aqueous alkali solution is circulated through a cathode cell (the fourth compartment $K_4$). A fermentation liquor is circulated through the third compartment $K_3$ partitioned by the anion exchange membranes, while an aqueous solution of an organic acid formed is circulated through the second compartment $K_2$ partitioned by the cation exchange membrane and the anion exchange membrane. A pH electrode (not shown in the figure) may be provided in the fermenter 2 to automatically supply electricity to the electrodialysis stack 4 when the prepared organic acid concentration increases to such an extent as to lower the pH below a range suitable for fermentation. When electricity is supplied to the electrodialysis stack, organic acid anions in the third compartment $K_3$ permeate through the anion exchange membrane $A_1$ on the side of the anode into the second compartment $K_2$, where the anions are neutralized with hydrogen ions entering the second compartment $K_2$ by permeation through the cation exchange membrane C from the anode cell $K_1$. In other words, organic acid anions in the fermentation liquor are easily recovered as a free organic acid into the aqueous organic acid solution (recovery liquid) in the second compartment.

This aqueous organic acid solution is discharged through overflow pipe 9 continuously. From this solution the organic acid is recovered by use of known procedures.

The fermentation broth in the third compartment $K_3$ is supplied with hydroxide anions through the anion exchange membrane $A_2$ to compensate the lost organic acid anions. This broth is circulated back to the fermenter 2 after the supply of the substrate and the nutrients through duct 1.

For level control within the fermenter and for control of cell density in the broth some broth is discharged from the broth cycle through duct 6. This part of broth is discharged totally or it is filtrated in a crossflow microfiltration unit (not shown in FIG. 1), the cells of the microorganismus being fed back to the broth and the cell free permeate only discharged.

The electric power is automatically switched off when the pH of the fermentation broth comes back to the adequate range.

FIG. 2 shows an EDS with three compartments only through which the same solutions as in FIG. 1 are circulated. In this EDS the compartment $K_4$ for the alkali solution cycle is omitted.

The fourth compartment $K_4$, the cathode cell shown in FIG. 1, is necessary to generate hydroxyl anions and to supply through the anion exchange membrane $A_2$ to the fermentation broth flowing through the third compartment $K_3$ when the contact of the broth with cathode causes any trouble.

On the other hand, then the direct contact of the broth with cathode makes no harm, the broth can be fed into the cathode compartment so as to generate the hydroxyl anions directly in the broth and the anion exchange membrane $A_2$ which separates $K_3$ and $K_4$ can be eliminated as well as the alkaline solution which circulates the $K_4$.

FIG. 3 shows an example for a multicompartment EDS. Through compartments $K1''$ and $K4''$ and the plurality of pairs of compartments $K2''$ and $K3''$ the same solutions are circulated as in FIG. 1. There may 10-100 pairs of compartments K2 and K3.

In all figures the ion exchange membranes are denoted as follows:
- A: anion exchange membrane
- C: cation exchange membrane
- CA: bipolar ion exchange membrane having a cation layer (C) and an anion layer (A)

In case the microorganism tends to give coatings on the membranes, the microorganism may be filtered off by crossflow microfiltration. So a fermentation broth freed from the microorganism will circle through the electrodialysis stack and back to the fermenter, and the microorganism will circle from the crossflow microfiltration unit directly back to the fermenter.

Thus, in the process of this invention, since cations are held in the fermentation liquor, no supplement of an alkali liquid is needed, and the lowered pH is restored to the suitable range only by recovering the formed organic acid from the fermentation liquor, whereupon the supply of electricity is automatically stopped. By contrast, in the ordinary electrodialysis which has heretofore been made, since cations as well as organic acid anions are separated out of the fermentation liquor, cations or an alkali solution disadvantageously is required to be supplemented to effect the pH adjustment. The fermentation liquor leaving the electrodialysis stack is returned to the fermenter after supplement of a substrate and a nutrient for the consumed ones. Thus a closed circuit is constituted where fermentation is continuously carried out.

Additionally stated, since the fermentation liquor containing the microorganism is directly passed through the electrodialysis stack, foreign bacteria, even if contained in the fermentation liquor, are prevented from growing. Thus they do not adversely affect the fermentation. Accordingly, although the fermenter and an initial fermentation medium must be sterilized to avoid contamination, a feed medium to be added to the system after the fermentation becomes vigorous following inoculation of the microorganism need not be sterilized.

ADVANTAGES OF THE INVENTION (1) Continuous fermentation can be conducted with a high organic acid productivity of 30 g/l·h or more.

(2) An aqueous solution of a free organic acid having a high concentration and a high purity can be easily and efficiently recovered from the organic acid fermentation liquor.

(3) An organic acid concentration of 30% or higher can be obtained.

(4) A high current efficiency of 90% or higher can be attained in electrodialysis.

(5) Labor and cost for removing the microorganism from the fermentation liquor can be omitted.

(6) Growth of foreign contaminating bacteria can be suppressed by recycling the fermentation liquor as such into the electrodialysis stack.

(7) Use of a neutralizing agent (base) for keeping the pH of the fermentation liquor suitable is not necessary.

EXAMPLE 1

A glass fermenter of 0.7 liter in capacity provided with a stirrer, a temperature sensor, a pH sensor, a liquid outlet, a liquid inlet, an overflow opening, an air vent communicated with a sterile filter, and a temperature control jacket was charged with 360 ml of a fermentation medium composed of 35 g/l of glucose, 10 g/l of yeast extracts (manufactured by Difco Inc.), 0.6 g/l of magnesium sulfate ($MgSO_4.7H_2O$), 0.03 g/l of manganese sulfate ($MnSO_4.4 \sim 5H_2O$), 0.03 g/l of ferrous sulfate ($FeSO_4.4H_2O$), 1 g/l of potassium phosphate monobasic, and 1 g/l of potassium phosphate dibasic. The feed was subjected, together with piping (Tygon PVC tube), to steam sterilization at 120° C. for 20 minutes. 50 ml of a lactic acid bacterium (*Lactobacillus delbrueckii* NRRL-B445) inoculum was inoculated in the medium, and the resulting mixture was kept anaerobic at 42±0.3° C. with stirring. After 9 hours, the dry weight of the microorganism was 3.2 g/l of cultured liquid, and lactic acid formed amounted to 25 g/l with the decrease in the remaining glucose to 7 g/l.

The fermenter was then aseptically connected with the third compartment of the electrodialysis stack (Du-ob manufactured by Asahi Glass Co. Ltd., effective membrane area: 1.7 dm$^2$). The fermentation liquor began to be circulated at a rate of 17 l/h, while at the same time the supplementary fermentation medium

| | |
|---|---|
| 378 g | glucose |
| 61 g | yeast extract |
| 1.5 g | $MgSO_4 \cdot 7 H_2O$ |
| 0.1 g | $MnSO_4 \cdot 5 H_2O$ |
| 0.1 g | $FeSO_4 \cdot 4 H_2O$ |
| 1 g | $K_2HPO_4$ |
| 1 g | $KH_2PO_4$ | began to be supplied to the fermenter at a rate of 0.1–0.6 ml/min.

The electrodialysis stack was composed of an anode, a cation exchange membrane (Neosepta® CMS manufactured by Tokuyama Soda Co. Ltd.), an anion exchange membrane (Neosepta® AMS), an anion exchange membrane (Neosepta® AM-3), and a cathode to form four compartments. A 18 g/l aqueous sulfuric acid solution, a 30 g/l aqueous lactic acid solution, and a 2 g/l aqueous caustic soda solution were circulated through the first compartment (anode cell), the adjacent second compartment, and the fourth compartment (cathode cell), respectively. The pH sensor in the fermenter was automatically set as to supply electricity to the electrodialysis stack when the pH of the medium reached 5.9 or below and stop the supply of electricity when the pH of the medium exceeded 6.1. In this way, the pH sensor controlled the pH of the fermentation liquor at 6.0±0.1. The voltage to be applied was manually controlled for a 6 hours' operation so that a time difference between each supply of electricity and stoppage thereof was not too long.

Whenever the electric current supplied to the EDS is switched on, the volume of the lactic acid solution in the cycle through compartment K2 increases. The excess solution of the lactic acid is discharged from this cycle by an overflow pipe and the pure lactic acid is recovered from this excess solution by evaporation.

During the continuous process some fermentation broth (about 0.05 to 0.4 ml/min) is discharged from its cycle.

The electric current was 1.3 amperes at the beginning and gradually increased with operation time lapse to reach 5.1 amperes just before the completion of the operation.

After 6 hours operation the productivity is 28 g lactic acid per liter of fermentation broth and hour. In the organic acid cycle the concentration is 173 g lactic acid per liter of solution. The yield of lactic acid is 95% based on the amount of glucose. The average current efficiency is 80%. The glucose concentration in the fermentation broth is maintained at about 2 g/l or more.

The concentration of the cell mass in the fermentation broth has increased to 8.2 g/l (calculated as dry cell mass).

EXAMPLE 2

The cell mass of *L. delbrueckii* is grown in the same way as in Example 1.

The bioreactor is connected with an EDS as shown in FIG. 1. The main characteristics of the EDS are:
  1.7 dm$^2$ effective membrane area,
  one cation exchange membrane (Neosepta CMS)
  one cation exchange membrane (Neosepta AM-3) and one anion exchange membrane (Selemion AMP) in this order from the side of the anode,
  sterilized with formaldehyde solution and rinsed with water free of microbes.

Through the four compartments of the EDS the following aqueous solutions are circulated:

| | |
|---|---|
| compartment | K1: 18 g/l sulfuric acid |
| | K2: 50 g/l lactic acid (initial concentration) |
| | K3: fermentation broth from bioreactor |
| | K4: 9 g/l sodium hydroxide |

A substrate solution (the composition of which is the same to that used in example 1) is prepared.

This substrate solution is fed continuously into the cycle of the fermentation broth at the entry of the bioreactor at a rate from 0.1 to 0.7 ml/min. Adding of NaOH solution is stopped. The fermentation broth is circulated through the EDS at a rate of 17 l/h.

The electric power supply of the EDS is automatically controlled by the pH sensor in the bioreactor. The power is switched on whenever the pH in the fermentation broth reaches 5.9; it remains switched on till the pH has increased to 6.1. Then the power is switched off and the pH in the fermentation broth again decreases to 5.9.

At the beginning of the continuous fermentation the electric current is 1.4 A. After 14 hours operation time steady state is reached and the electric current is about 5.4 A. After 14 hours, the concentration of the cell mass in the fermentation broth has increased to 11 g/l (calculated as dry cell mass).

Whenever the electric current supplied to the EDS is switched on, the volume of the lactic acid solution in the cycle through compartment K2 increases. The excess solution of the lactic acid is discharged from this cycle by an overflow pipe and the pure lactic acid is recovered from this excess solution by evaporation.

During the continuous process some fermentation broth (about 0.05 to 0.4 ml/min) is discharged from its cycle.

Under steady state conditions the productivity is 35 g lactic acid per liter of fermentation broth and hour. In the organic acid cycle the concentration is 240 g lactic acid per liter of solution. The yield of lactic acid is 96% based on the amount of glucose. The average current efficiency is 93%. The glucose concentration in the fermentation broth is maintained at about 2 g/l or more. Sterilization of the substrate feed is omitted, but no growth of foreign bacteria is observed.

This proved that the bactericidal effect of EDS was strong enough to calm down the alien bacterias introduced by contamination, at the same time not so strong as to influence the normal activities of the dominant bacteria, Lactobacillus delbruekii, and that the trouble some anticontamination device and care could be eliminated.

EXAMPLE 3

The cell mass of *L. delbrueckii* is grown in the same way as in Example 1.

The bioreactor is connected with an EDS as shown in FIG. 2. The main characteristics of the EDS are:
1.7 dm² effective membrane area
one cation exchange membrane (Neosepta CMS)
one anion exchange membrane (Neosepta AM-3) in this order from the side of the anode,
sterilized with formaldehyde solution and rinsed with water free of microbes.

Through the three compartments of the EDS the following aqueous solutions are circulated:

| compartment | K1: 18 g/l sulfuric acid |
|---|---|
| | K2: 50 g/l lactic acid (initial concentration) |
| | K3: fermentation broth from bioreactor |

The same substrate solution as in Example 1 is fed continuously into the cycle of the fermentation broth at the entry of the bioreactor at a rate from 0.1 to 0.6 ml/min. Adding of NaOH solution is stopped. The fermentation broth is circulated through the EDS at a rate of 17 g/l.

The electric power supplied to the EDS is switched on and off in the same way as in Example 1.

After 13 hours operation time the cell mass in the fermentation broth has a concentration of 16 g/l (calculated as dry mass).

Excess solution of lactic acid and some fermentation broth is discharged in the same way as indicated in Example 1, Part B.

Under steady state conditions the productivity is 19 g lactic acid per liter of fermentation broth and hour. In the organic acid cycle the concentration is 187 g lactic acid per liter of solution. The yield of lactic acid is 84% based on the amount of glucose. The average current efficiency is 70%. The glucose concentration in the fermentation broth is maintained at about 2 g/l or more.

We claim:

1. A continuous process for the fermentative preparation of organic acids comprising passing a fermentation broth from a fermenter through an electrodialysis unit and back to the fermenter to recover a solution of organic acids wherein said electrodialysis is conducted in an electrodialysis unit having three compartments separated from each other by a cation exchange membrane and an anion exchange membrane in this order from the side of an anode.

2. The process of claim 1, comprising circulating an acid through compartment K1, a product acid through compartment K2 and the fermentation broth through compartment K3 and recovering the product acid from the solution flowing through commpartment K2.

3. A continuous process for the fermentative preparation of organic acids comprising passing a fermentation broth from a fermenter through an electrodialysis unit and back to the fermenter to recover a solution of organic acids wherein said electrodialysis is conducted in an electrodialysis unit having four compartments separated from each other by a cation exchange membrane and two anion exchange membranes in this order from the side of an anode.

4. The process of claim 3 comprising circulating an acid through compartment K1, the fermentatively prepared organic acid through compartment K2, the fermentation broth through compartment K3 and an alkaline solution through compartment K4 and recovering the acid from the solution flowing through compartment K2.

5. A continuous process for the fermentative preparation of organic acids comprising passing a fermentation broth from a fermenter through an electrodialysis unit and back to the fermenter to recover a solution of organic acids wherein said electrodialysis is conducted in a series of electrodialysis units having one anode compartment K1, a series of compartment pairs K2 and K3 and one cathode compartment K4, separated from each other by a cation exchange membrane, an anion exchange membrane, a series of pairs of bipolar membranes and an anion exchange membrane, and an anion exchange membrane in this order from the side of an anode.

6. The process of claim 5 comprising circulating an acid through compartment K1, the fermentatively prepared organic acid through compartment K2, the fermentation broth through compartment K3 and an alkaline solution through compartment K4 and separating the fermentatively prepared organic acid from the solution flowing through compartment K2.

7. The process of claim 5 or 6 comprising conducting said electrodialysis in a device having 10 to 100 pairs of compartments K2 and K3.

8. The process of claim 2, 4 or 6 wherein said acid in compartment K1 is sulfuric acid at a concentration of 0.1 to 10% and that said alkaline solution in compartment K4 is sodium hydroxide at a concentration of 0.01 to 10%.

* * * * *

UNITED STATES PATENT AND TRADEMARK OFFICE
CERTIFICATE OF CORRECTION

PATENT NO. : 4,882,277

DATED : November 21, 1989

INVENTOR(S) : Czytko et al.

It is certified that error appears in the above-identified patent and that said Letters Patent is hereby corrected as shown below:

Column 1, line 45, "form" should be --from--.

Signed and Sealed this

Fourth Day of December, 1990

Attest:

HARRY F. MANBECK, JR.

*Attesting Officer*  *Commissioner of Patents and Trademarks*